United States Patent [19]

Gould et al.

[11] Patent Number: 5,550,141
[45] Date of Patent: Aug. 27, 1996

[54] METHOD FOR INHIBITING THE FORMATION OF ACID MINE DRAINAGE

[75] Inventors: W. Douglas Gould, Ottawa; Lyne Lortie; Geneviève Béchard, both of Hull, all of Canada

[73] Assignee: Natural Resources - Canada, Ottawa, Canada

[21] Appl. No.: 522,450

[22] Filed: Aug. 31, 1995

[51] Int. Cl.$^6$ .......................... A01N 43/82; A01N 43/50; C02F 3/00
[52] U.S. Cl. ........................ 514/363; 514/392; 210/601
[58] Field of Search ........................ 514/363, 392; 210/601

[56] References Cited

U.S. PATENT DOCUMENTS

| | | | |
|---|---|---|---|
| 3,106,525 | 10/1963 | Schmid et al. | 210/57 |
| 3,551,349 | 12/1970 | Kallfass et al. | 252/392 |
| 3,882,018 | 5/1975 | Depree | 210/20 |
| 4,282,111 | 8/1981 | Ciuba | 252/178 |
| 4,306,988 | 12/1981 | Rothgery | 252/150 |
| 4,329,475 | 5/1982 | Rothgery | 548/141 |
| 4,406,811 | 9/1983 | Christensen et al. | 252/180 |
| 4,541,932 | 9/1985 | Muccitelli | 210/750 |
| 4,561,948 | 12/1985 | Stiller | 204/129 |
| 4,695,378 | 9/1987 | Ackman et al. | 210/198.1 |
| 5,076,927 | 12/1991 | Hunter | 210/603 |
| 5,078,899 | 1/1992 | Garrison | 210/704 |
| 5,171,454 | 12/1992 | Bockowski et al. | 210/764 |
| 5,256,311 | 10/1993 | Rossi et al. | 210/750 |
| 5,259,975 | 11/1993 | Mohn | 210/710 |
| B1 4,278,635 | 7/1988 | Kerst | 422/14 |

*Primary Examiner*—Raymond Henley, III

[57] ABSTRACT

A method is described for inhibiting the production of acid mine drainage from the disposal of sulphide tailings and waste rock deposition during mining and milling of sulphide containing ores, which comprises adding to said sulphide tailings or waste rock deposition an effective amount of 2-mercapto-1-methyl imidazole or a 1,3,4-thiadiazole selected from the group consisting of 2,5-dimercapto-1,3,4-thiadiazole and 5-amino-2-thiol-1,3,4-thiadiazole to inhibit oxidation of sulphides and thereby prevent the formation of acid mine drainage.

5 Claims, 2 Drawing Sheets

METHOD FOR INHIBITING THE FORMATION OF ACID MINE DRAINAGE

FIELD OF THE INVENTION

This invention relates to methods for inhibiting the formation of "acid mine drainage" i.e. acidic waste water, in mining and mineral processing operations.

BACKGROUND OF THE INVENTION

The production of acidic drainage from reactive sulphidic tailings and waste rock deposition produced during mining and milling of sulphide containing ores is a major ecological problem. This acid mine drainage can have devastating effects on receiving waters.

Acid mine drainage is the result of both the biotic and abiotic oxidation of sulfide minerals typically found in tailings ponds and waste rock dumps. The acid mine drainage typically has a low pH, high gulfate content and contains high concentrations of dissolved metals which can be detrimental to the biota in receiving waters.

The processes involved in the initiation of acid generation are not well understood. The autotrophic thiobacilli are capable of oxidizing a number of metal gulfides to produce gulfuric acid and solubilize metals. Some researchers have suggested that a succession of pH-dependent microbial activities was responsible for establishing the acidic conditions required for growth of the sulfur- and iron-oxidizing bacteria responsible for the production of acid mine drainage. It has been postulated that acidification of pyrite occurs in three stages and that both biotic and abiotic reactions occur in the first stage with the abiotic processes predominating (above pH 4.5). During the last two stages (below 4.5) biological reactions predominate. The most well characterized of the acidophilic thiobacilli is *Thiobacillus ferrooxidans* which has a pH range for growth between 1.0 and 4.0. At pH values lower than 4.5, iron oxidizing bacteria such as *T. ferrooxidans* catalyze the oxidation of ferrous iron in both the soluble and the mineral phase to ferric iron. At pH 3.0 the bacterial oxidation of ferrous iron is $10^6$ times more rapid than the chemical oxidation.

Although the role of microbial activity in initiating the oxidation of tailings was previously not considered to be important, more recent research has shown that bacteria are involved in the initial oxidation stage. A number of Thiobacillus species are capable of rapid growth at neutral pH values commonly found in fresh tailings. *Thiobacillus thioparus* is active over a pH range of 6.0 to 8.0 and can oxidize a number of reduced sulfur compounds such as elemental sulfur, sulfide, sulfite, thiosulfate and thiocyanate. *Thiobacillus novellus* is active over the pH range of 6.0 to 8.0 and can grow on either organic or inorganic substrates.

Amelioration of acid mine drainage can be accomplished by either preventing the generation of acid mine drainage or treating the effluent after it has been produced. Techniques for the prevention of acid mine drainage include the use of both wet and dry covers. Another approach has been to use bacterial inhibitors active against *T. ferrooxidans*, such as acrolein as described in Bockowski et al, U.S. Pat. No. 5,171,454. At low pH values artionic surfactants are bactericidal. Surfactants alone have a limited lifetime due to dilution and leaching. Slow-release rubber-based surfactant pellets that should extend the effective lifetime of these agents have been developed. More recently, longer term field data has shown that the use of inhibitors significantly reduced the generation of acid mine drainage in materials such as overburden, coal refuse and metal mine waste rock. Another approach would be to use compounds that inhibit the bacteria involved in the initial phases of the oxidation of tailings. The inhibitors would prevent oxidation during the period that they are exposed to oxygen until a wet or dry cover can be applied.

Thiol-binding reagents such as N-ethyl maleimide and iodoacetamide have been shown to block the oxidation of thiosulfate to sulfate by *Thiobacillus neapolitanus*. Glutathione is involved in the oxidation of thiosulfate by other species of thiobacilli via the formation of glutathione polysulfides which are subsequently oxidized to produce sulfite. The oxidation of elemental sulfur by *Thiobacillus thiooxidans* can be blocked by the addition of N-ethyl maleimide. Thus, numerous studies have shown the involvement of thiol groups in the oxidation of sulphur and thiosulfate by various thiobacilli. The use of thiol blocking reagents to inhibit the initial steps of sulfur oxidation that occur at higher pH values is another potential strategy for the prevention of acid mine drainage. However, many of the thiol blocking compounds such as N-ethyl maleimide are relatively toxic.

U.S. Pat. Nos. 4,306,988 and 4,329,495 describe two 1,3,4-thiadiazole derivatives that are effective corrosion inhibitors in acid metal-treating baths. However, the two patents describe the 1,3,4-thiadiazoles in the form of poly-(oxyalkylated) derivatives. These derivatives are described as having low toxicity, but are not effective for inhibiting the formation of acid mine drainage.

It is the object of the present invention to find compounds which are capable of inhibiting the formation of acid mine drainage while also having low toxicity.

SUMMARY OF THE INVENTION

According to the present invention, it has surprisingly been discovered that there are 1,3,4-thiadiazole compounds which are low in toxicity and which are highly effective in inhibiting the production of acid mine drainage by blocking the oxidation of sulphur compounds to sulphates. Two thiadiazole compounds of particular interest are 5-amino-1,3,4-thiadiazole-2-thiol and 2,5-dimercapto-1,3,4-thiadiazole. A related thiol compound also useful is 2-mercapto-1-methyl imidazole. Further advantages may be found by using a mixture of two or more of the above inhibitors. It has been found that while the derivatives described in U.S. Pat. Nos. 4,306,988 and 4,329,475 do not function as inhibitors within the environment of the present invention, the compounds of the present invention are surprisingly highly effective.

The inhibitors of the invention are typically mixed with the tailings or applied to the rock surfaces of a waste rock deposition. A solution of the inhibitors may be mixed with a slurry of tailings or a dilute solution may be sprayed onto the surface of the waste rock. when mixed with the tailings, the inhibitors are present in concentrations of usually greater than 0.1 part per million parts of tailings and preferably about 100 to 500 parts per million. It is not necessary to apply the inhibitors to all tailings, but only to those to be stored in unsaturated conditions where they are exposed to oxygen. Whether the inhibitors are being mixed with the tailings or sprayed on the rock surfaces, the concentrations required can vary greatly depending on individual circumstances. The actual amounts needed in each situation to effectively inhibit production of acid mine drainage can easily be determined by simple routine tests.

Thorough mixing of the inhibitor with the tailings is, of course, important. In typical operations, mine tailings are formed into a slurry which is pumped to a tailings pond for storage. It is particularly convenient to add the inhibitor during slurrying because this provides very effective mixing.

BRIEF DESCRIPTION OF THE DRAWINGS

In the drawings which illustrate preferred embodiments of the invention.

DESCRIPTION OF THE PREFERRED EMBODIMENTS

EXAMPLE 1

Materials and Methods

Tailings:

Unoxidized tailings obtained from several sources were homogenized by manually mixing. The mixed tailings had the composition shown in Table 1 below:

TABLE 1

| Elements | Content in % (w/w) |
|---|---|
| Fe | 20.8 ± 0.72 |
| Total S | 10.2 ± 0.31 |
| $SO_4^{2-}$ | 2.3 ± 0.10 |
| Ca | 2.3 ± 0.08 |
| Mg | 1.6 ± 0.04 |
| Zn | 0.58 ± 0.042 |
| $PO_4$ | 0.14 ± 0.015 |
| Pb | 0.09 ± 0.050 |
| Cu | 0.08 ± 0.007 |
| Na | 0.08 ± 0.0004 |
| Co | 0.02 ± 0.0002 |
| Cd | 0.00 ± 0.003 |
| Ni | 0.00 ± 0.000 |
| Ag | 0.00 ± 0.000 |

Four subsamples were air dried and ground and then subsequently analyzed for Fe, total S, $SO_4^{2-}$, Ni, Co, Cu, Zn, Ca, Mg, Na, Ag, Pb, Cd and $PO_4$.

Column Preparation:

Three treatments in triplicate were used; control without inhibitors and two different inhibitors, 5-amino-2-thiol-1,3,4-thiadiazole or 2,5-dimercapto-1,3,4-thiadiazole (Aldrich Chemical Company, Milwaukee, Wis.). A total of nine columns (6.2 cm I.D.×31 cm height) were packed with 2 kg wet weight of homogenized unoxidized tailings. The bottom of each column was packed with quartz (¼") and covered with glass wool and additional quartz to retain the glass wool in place. A volume of 500 mL of tap water was added to each column before the tailings were added. A slurry consisting of 2 L of tap water and 2 kg of homogenized unoxidized tailings was mixed and poured in the columns. The tailings were allowed to settle and drain overnight; excess water at the top of each column was removed by siphoning.

The remainder of the tailings was added the following day and allowed to drain for two days. Inoculum, prepared by mixing 50 mL of medium B ATCC #238 (Gherna et al. 1989) with 20 g of oxidized tailings containing microorganisms, was added to each column and allowed to drain for 24 h. The following day 100 mL of slurry containing 1 g of inhibitor was added to the respective columns to a final inhibitor concentration in the tailings of 500 µg/g (w/w). A 100 mL volume of tap water was added to each of the control columns.

Figure 1:
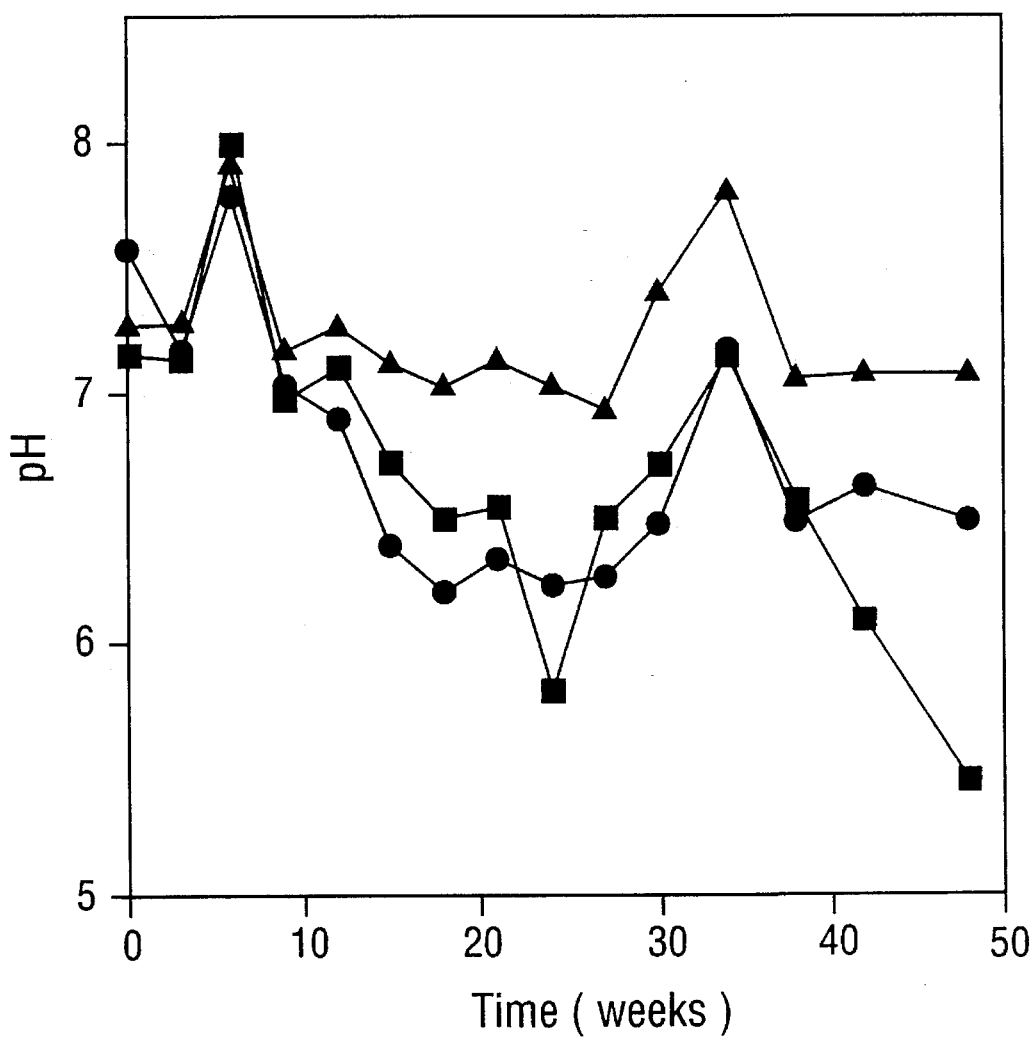
FIG. 1 is a plot of pH vs. time.
Figure 2:
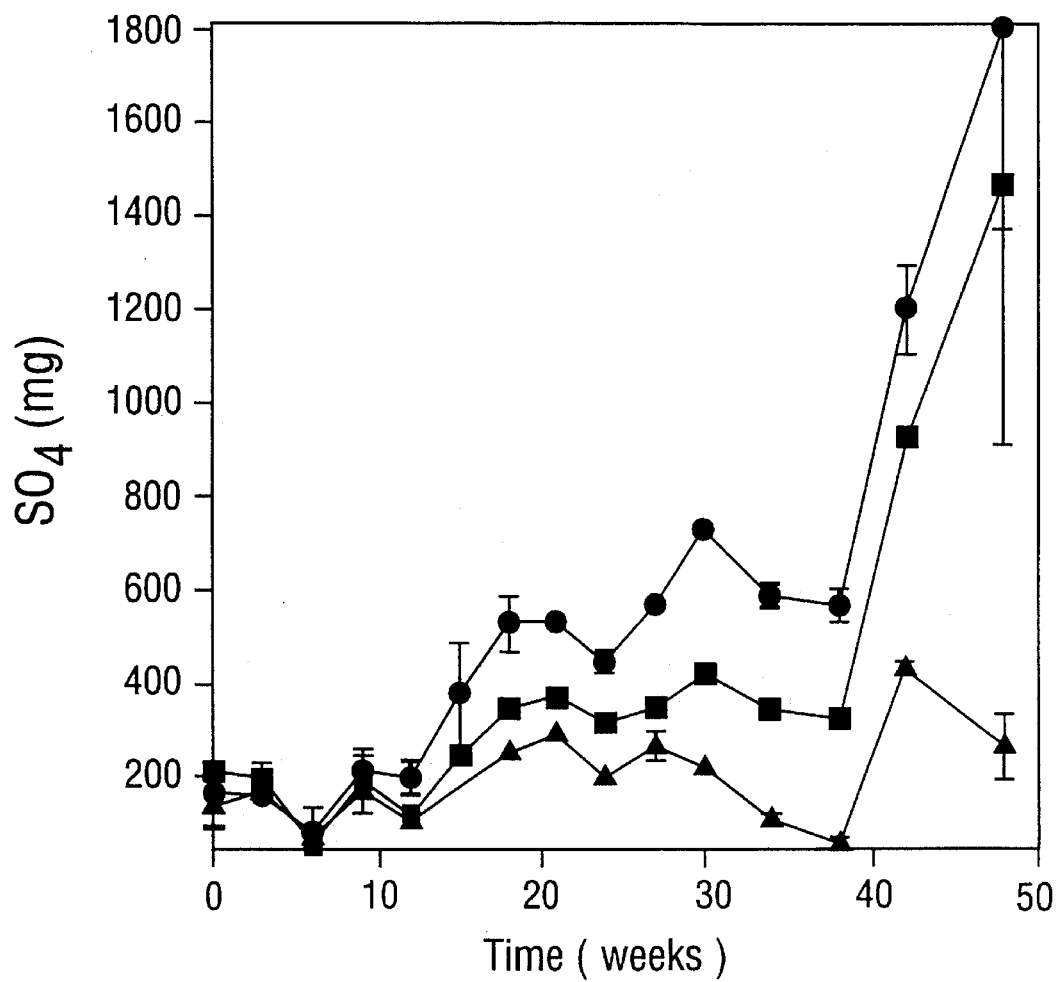
FIG. 2 is a plot of $SO_4$ content vs. time.

Sampling:

Every three weeks, 150 mL of tap water was added to each of the columns. The columns were sampled after adding the inhibitor preparation or tap water: they were allowed to drain for 24 h and the eluates were collected. The pH values of the eluates were measured; they were then acidified with 4 N HCl and saved for analysis. The measured pH values are shown in FIG. 1, while the $SO_4$ contents obtained are shown in FIG. 2.

During the initial 20 weeks both inhibitors suppressed the decline in pH that was observed in the leachate from the control columns. However, between 20 and 50 weeks, 2,5-dimercapto-1,3,4-thiadiazole was less effective than either the control or the other inhibitor in preventing the leachate pH decline. 5-amino-2-thiol-1,3,4-thiazdiazole was effective in preventing the pH decline in the leachate for the duration of the experiment. The oxidation of metal sulfides produces soluble metals, acidity and soluble sulfate.

The sulfate content of the leachate is also an indication of the amount of bacterial oxidation that has occurred. The sulfate data in FIG. 2 show similar trends as the pH data. The graphs showing sulfate indicate the total quantity of sulfate leached from the columns during each leaching event. During a 60 week period the largest quantity of sulfate produced was from the control columns (12.769 g in total) and the columns treated with 2,5-dimercapto-1,3,4-thiadiazole (8.242 g in total) and the lowest amount being leached from the columns treated with 5-amino-2-thiol-1,3,4-thiadiazole (4.580 g in total). It is believed that the dimercapto compound is less effective than the amino compound because of the low solubility of the dimercapto compound. The inhibitors were added to the surface of the columns as a slurry and then leached downwards during each leaching event.

EXAMPLE 2

Experimental Design:

An experiment using shake flask cultures and tailings was used to evaluate three inhibitors alone and various combinations of the inhibitors for the inhibition of acid mine drainage.

The tailings used had the compositions shown in Table 2 below:

TABLE 2

| Element | % composition |
|---|---|
| Ag | 0.07 |
| Al | 0.1 |
| As | 0.55 |
| Au | NF* |
| B | NF |
| Ba | 0.4 |
| Be | 0.065 |
| Ca | 1.7 |
| Cd | 0.01 |
| $Co_3$ | 4.45 |
| CO | 0.025 |
| Cr | 0.02 |
| Cu | 0.07 |
| Fe | 31.5 |
| Ga | NF |
| Ge | NF |
| Mg | 0.4 |
| Mn | 0.01 |
| Mo | NF |
| Na | 0.14 |

TABLE 2-continued

| Element | % composition |
|---|---|
| Nb | 0.06 |
| Ni | NF |
| Pb | 1.2 |
| S | 33.5 |
| Sb | 0.2 |
| Se | NF |
| Si | 6.1 |
| Sn | NF |
| Sr | 0.01 |
| Ti | 0.06 |
| V | NF |
| Zn | 1.6 |

*Not Found

To 250 mL Erlenmeyer flasks (in triplicate) were added 85 mL of a salts medium used for the culture *Thiobacillus thioparus*, 5.0 mL of a culture of *T. thioparus* (ATCC #23645), 10.0 mL of inhibitor(s) dissolved in the same medium, 20 g of fresh tailings and 0.5 g of oxidized tailings as an additional source of sulfur oxidizing bacteria. The *T. thioparus* medium had the following composition in g/L: 0.95 $Na_2HPO_4$; 1.2 $KH_2PO_4$; 0.2 $MgCl_2$; 1.0 $NH_4Cl$; 0.006 $FeCl_3$; and 0.015 $CaNO_3$. The inhibitors were added either singly or in combination at two different concentrations; 400 ppm total inhibitor (alone or combined) and 200 ppm total inhibitor. After the inhibitors and bacterial inocula were added, the flasks were incubated in a constant temperature incubator with a rotary shaker with shaking at 150 RPM and at 28° C. Samples were taken at the beginning of the experiment and after four weeks of incubation. The sulfate concentrations were determined by high performance ion chromatography.

The degree of inhibition was calculated in the following way:

$$\% \text{ Inhibition} = \frac{\text{Control (SO}_4) - \text{Sample (SO}_4)}{\text{Control (SO}_4)} \times 100$$

Control $(SO_4)$=Sulfate produced in the control flasks during the four week incubation period.

Sample $(SO_4)$=Sulfate produced in the flasks containing inhibitor during the four week incubation period.

The results obtained are shown in Table 3 below:

TABLE 3

| Compound | Total Inhibitor Concentration, ppm | % Inhibition |
|---|---|---|
| 1. DMT | 400 | 61 |
| 2. AT | 400 | 35 |
| 3. MI | 400 | 0 |
| 4. AT + DMT | 400 | 50 |
| 5. AT + MI | 400 | 19 |
| 6. DMT + MI | 400 | 48 |
| 7. AT + DMT | 200 | 20 |
| 8. AT + MI | 200 | 0 |
| 9. DMT + MI | 200 | 24 |

DMT: 2,5-dimercapto-1,3,4-thiadiazole
AT: 5-amino-2-thiol-1,3,4-thiadiazole
MI: 2-mercapto-1-methylimidazole

We claim:

1. A method for inhibiting the production of acid mine drainage from the disposal of sulphide tailings and waste rock deposition during mining and milling of sulphide containing ores, which comprises adding to said sulphide tailings or waste rock deposition an effective amount of (i) 2-mercapto-1-methyl imidazole or (ii) a 1,3,4-thiadiazole selected from the group consisting of 2,5-dimercapto-1,3,4-thiadiazole and 5-amino-2-thiol-1,3,4-thiadiazole to inhibit oxidation of sulphides and thereby prevent the formation of acid mine drainage.

2. A method according to claim 1 wherein a mixture of at least two of said inhibiting compounds is used.

3. A method according to claim 1 wherein the inhibiting compound is thoroughly mixed with a slurry of tailings.

4. A method according to claim 3 wherein the inhibiting compound is mixed with the slurry in a concentration of about 100–500 parts per million parts of tailings.

5. A method according to claim 1 wherein a dilute aqueous solution of the inhibiting compound is sprayed onto rock surfaces of the waste rock deposition.

* * * * *